(12) United States Patent
Zhu (10) Patent No.: US 10,111,469 B2
(45) Date of Patent: Oct. 30, 2018

(54) VAPORIZERS HAVING TOP AIR INTAKE AND ELECTRONIC CIGARETTE HAVING THE SAME

(71) Applicant: Xiaochun Zhu, Shenzhen (CN)

(72) Inventor: Xiaochun Zhu, Shenzhen (CN)

(73) Assignee: SHENZHEN KANGER TECHNOLOGY CO., LTD., Shenzhen (CN)

( * ) Notice: Subject to any disclaimer, the term of this patent is extended or adjusted under 35 U.S.C. 154(b) by 210 days.

(21) Appl. No.: 15/201,635

(22) Filed: Jul. 5, 2016

(65) Prior Publication Data
US 2018/0007961 A1 Jan. 11, 2018

(51) Int. Cl.
A24F 47/00 (2006.01)
B65B 3/04 (2006.01)
F16J 15/02 (2006.01)
H05B 3/42 (2006.01)

(52) U.S. Cl.
CPC ............ *A24F 47/008* (2013.01); *B65B 3/04* (2013.01); *F16J 15/021* (2013.01); *H05B 3/42* (2013.01); *H05B 2203/021* (2013.01)

(58) Field of Classification Search
CPC ......... A24F 47/008; B65B 3/04; F16J 15/021; H05B 3/42; H05B 2203/021
USPC .................................................. 131/329, 328
See application file for complete search history.

(56) References Cited

U.S. PATENT DOCUMENTS

| 9,795,169 B1* | 10/2017 | Zhu ........................ A24F 47/008 |
| 2012/0167906 A1* | 7/2012 | Gysland ................ A24F 47/008 131/328 |
| 2014/0366898 A1* | 12/2014 | Monsees ............... A24F 47/008 131/329 |
| 2015/0059787 A1* | 3/2015 | Qiu ........................ A24F 47/008 131/329 |
| 2015/0196059 A1* | 7/2015 | Liu ........................ A24F 47/008 131/329 |
| 2016/0000147 A1* | 1/2016 | Li ........................... A24F 47/008 131/329 |
| 2016/0015081 A1* | 1/2016 | Liu ........................... H05B 3/16 131/329 |

(Continued)

*Primary Examiner* — Tulsidas C Patel
*Assistant Examiner* — Travis Chambers
(74) *Attorney, Agent, or Firm* — Ming Jiang; MM IP Services LLC (57) ABSTRACT

Electronic cigarettes may include an electronic cigarette, and a replaceable vaporizer assembly. Electronic cigarette may include an electronic cigarette body, and a replaceable vaporizer assembly. In certain embodiments, the electronic cigarette body may include a mouthpiece, an E-liquid storage tank, an E-liquid refill cap, a mounting ring, a connector, and a vaporizer mounting base having an internal thread. The replaceable vaporizer assembly may include an external thread of a vaporizer assembly base. The replaceable vaporizer assembly may be replaced by removing the mouthpiece, unscrewing the replaceable vaporizer assembly to detach the external thread of the vaporizer assembly base from the internal thread of the vaporizer mounting base, pulling up the replaceable vaporizer assembly, replacing a new replaceable vaporizer assembly, and reinstalling the mouthpiece back in place. The electronic cigarette includes a top adjustable air intake. The mouthpiece may be used to adjust the air intake by rotating the mouthpiece.

19 Claims, 6 Drawing Sheets

(56) References Cited

U.S. PATENT DOCUMENTS

2016/0015082 A1\* 1/2016 Liu ..................... A24F 47/008
    131/329
2016/0332754 A1\* 11/2016 Brown ..................... B65B 3/10

\* cited by examiner

VAPORIZERS HAVING TOP AIR INTAKE AND ELECTRONIC CIGARETTE HAVING THE SAME

FIELD

The present disclosure generally relates to the field of electronic cigarette, and more particularly to replaceable vaporizer assemblies having top adjustable air intake and electronic cigarettes having the replaceable vaporizer assemblies having top adjustable air intake.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

It is well known that smoking cigarette is harmful to smoker's health. The active ingredient in a cigarette is mainly nicotine. During smoking, nicotine, along with tar aerosol droplets produced in the cigarette burning, are breathed into the alveolus and absorbed quickly by the smoker. Once nicotine is absorbed into the blood of the smoker, nicotine then produces its effect on the receptors of the smoker's central nervous system, causing the smoker relax and enjoy an inebriety similar to that produced by an exhilarant.

The electronic cigarette is sometimes referred as electronic vaporing device, personal vaporizer (PV), or electronic nicotine delivery system (ENDS). It is a battery-powered device which simulates tobacco smoking. It generally uses a heating element that vaporizes a liquid solution (e-liquid). Some solutions contain a mixture of nicotine and a variety of flavorings, while others release a flavored vapor without nicotine. Many are designed to simulate smoking experience, such as cigarette smoking or cigar smoking. Some of them are made with similar appearance, while others are made considerably different in appearance.

Replacing a vaporizer in a conventional electronic cigarette is difficult. When E-liquid gets on the vaporizer while someone is replacing the vaporizer, he/she may be contaminated with E-liquid, and it is hard to clean. Therefore, it is desirable to replace the vaporizer easily without getting E-liquid contamination.

Therefore, an unaddressed need exists in the art to address the aforementioned deficiencies and inadequacies.

SUMMARY

In one aspect, the present disclosure relates to a replaceable vaporizer assembly for electronic cigarettes. In certain embodiments, the replaceable vaporizer assembly may include: a top vapor tube mount, an air intake tube, a vapor tube, a connecting ring, an E-liquid storage medium, a heating element, and a vaporizer assembly base. In certain embodiments, the air intake tube may define a first air intake opening, a second air intake opening, a first E-liquid opening, and a second E-liquid opening. The heating element may include a positive terminal and a negative terminal. The vaporizer assembly base may define a first air gap, a second air gap, a first E-liquid opening, and a second E-liquid opening. The heating element is installed inside the E-liquid storage medium. The E-liquid storage medium is installed inside the vaporizer assembly base between the connecting ring and the vaporizer assembly base. In certain embodiments, the vapor tube is positioned inside the air intake tube between the top vapor tube mount and the connecting ring to form a cylindrical space between the vapor tube and the air intake tube, wherein an air passage is formed to provide air into an inside of the heating element through the first air intake opening and the second air intake opening, the cylindrical space between the vapor tube and the air intake tube, the first air gap and the second air gap.

In another aspect, the present disclosure relates to an electronic cigarette body. In certain embodiments, the electronic cigarette body may include: a mouthpiece, an E-liquid storage tank, an E-liquid refill cap, a connector, a mounting ring, and a vaporizer mounting base. In certain embodiments, the E-liquid storage tank may include a top end and a bottom end. The E-liquid refill cap is positioned on the top end of the E-liquid storage tank. The mounting ring may include an internal thread. The external thread of the E-liquid refill cap is configured to threadedly connect to the internal thread of the mounting ring. In certain embodiments, the E-liquid storage tank may be positioned between the E-liquid refill cap and the vaporizer mounting base. The E-liquid storage tank may be sealed by a first sealing ring between the E-liquid refill cap on the top end of the E-liquid storage tank and a second sealing ring between the bottom end of the E-liquid storage tank and the vaporizer mounting base. The E-liquid in the E-liquid storage tank is in communication with an E-liquid storage medium through a first E-liquid opening and a second E-liquid opening of the air intake tube. In certain embodiments, the E-liquid storage tank is configured to store E-liquid between the top end and the bottom end of the E-liquid storage tank. When refilling E-liquid, a user may remove the mouthpiece, unscrew the E-liquid refill cap to detach the external thread of the E-liquid refill cap from the internal thread of the mounting ring to open the top and of the E-liquid storage tank, and refill E-liquid into the E-liquid storage tank from the opened top end of the E-liquid storage tank.

In yet another aspect, the present disclosure relates to an electronic cigarette. In certain embodiments, the electronic cigarette may include: an electronic cigarette body, and a replaceable vaporizer assembly. In certain embodiments, the electronic cigarette body may include a mouthpiece, an E-liquid storage tank, an E-liquid refill cap, a mounting ring, a connector, and a vaporizer mounting base having an internal thread. The replaceable vaporizer assembly may include an external thread of a vaporizer assembly base. The replaceable vaporizer assembly may be replaced by removing the mouthpiece, unscrewing the replaceable vaporizer assembly to detach the external thread of the vaporizer assembly base from the internal thread of the vaporizer mounting base, pulling up the replaceable vaporizer assembly, replacing a new replaceable vaporizer assembly, and reinstalling the mouthpiece back in place.

These and other aspects of the present disclosure will become apparent from the following description of the preferred embodiment taken in conjunction with the following drawings, although variations and modifications therein may be effected without departing from the spirit and scope of the novel concepts of the disclosure.

BRIEF DESCRIPTION OF THE DRAWINGS

The accompanying drawings illustrate one or more embodiments of the disclosure and, together with the written description, serve to explain the principles of the disclosure. Wherever possible, the same reference numbers are used throughout the drawings to refer to the same or like elements of an embodiment. The drawings do not limit the present disclosure to the specific embodiments disclosed and described herein. The drawings are not necessarily to scale, emphasis instead being placed upon clearly illustrating the principles of the disclosure, and wherein.

DETAILED DESCRIPTION

The present disclosure will now be described more fully hereinafter with reference to the accompanying drawings, in which exemplary embodiments of the disclosure are shown. This disclosure may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom", "upper" or "top," and "front" or "back" may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximates, meaning that the term "around", "about" or "approximately" can be inferred if not expressly stated.

Many specific details are provided in the following descriptions to make the present disclosure be fully understood, but the present disclosure may also be implemented by using other manners different from those described herein, so that the present disclosure is not limited by the specific embodiments disclosed in the following.

The description will be made as to the embodiments of the present disclosure in conjunction with the accompanying drawings FIGS. 1 through 6.

Figure 1:
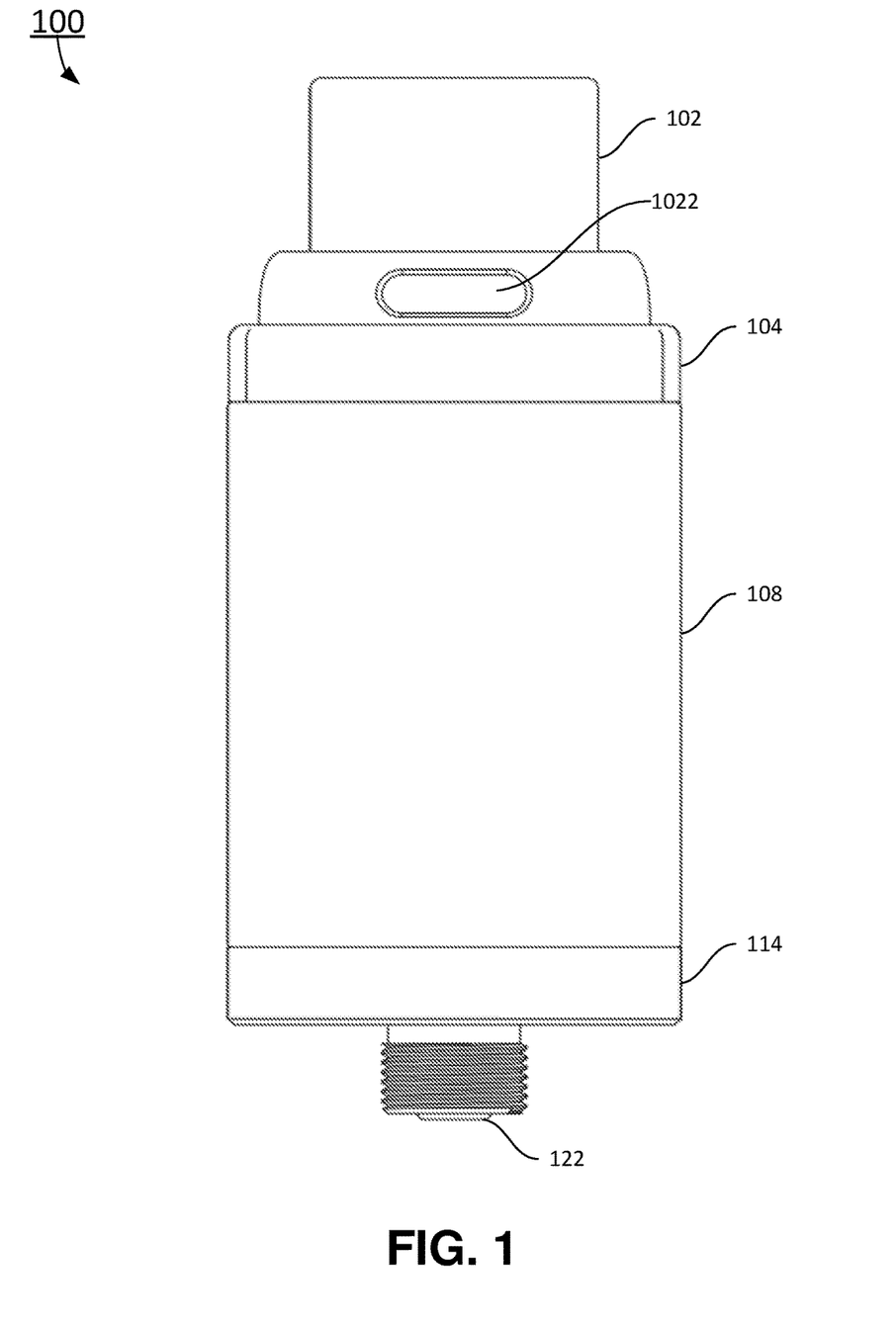
FIG. 1 is an external view of an exemplary electronic cigarette having a replaceable vaporizer assembly and a top adjustable air intake according to certain embodiments of the present disclosure.

Referring now to FIG. 1, an external view of an exemplary electronic cigarette 100 is shown according to certain embodiments of the present disclosure. The electronic cigarette 100 includes multiple distinctive features of present disclosure: an easy replaceable vaporizer assembly, an easy E-liquid refilling mechanism, and a top adjustable air intake for the electronic cigarette 100. In certain embodiments, the electronic cigarette 100 may include: a mouthpiece 102, an E-liquid refill cap 104, an E-liquid storage tank 108, a vaporizer mounting base 114, and a positive terminal 122 of a power connector. The mouthpiece 102 may be removed from top of the electronic cigarette 100 to replace a replaceable vaporizer assembly (not shown in FIG. 1). The E-liquid refill cap 104 may be threadedly removed to refill E-liquid into the E-liquid storage tank 108. The mouthpiece 102 may define a first air intake opening 1022 which overlaps with a first air intake opening 2041 of an air intake tube 204 (not shown in FIG. 1) and a second air intake opening 1023 which overlaps with a second air intake opening 2042 of the air intake tube 204 (not shown in FIG. 1) such that when a user rotates the mouthpiece 102 to a first predetermined angle, the first air intake opening 1022 of the mouthpiece 102 aligns with the first air intake opening 2041 of the air intake tube 204, and the second air intake opening 1022 of the mouthpiece 102 aligns with the second air intake opening 2042 of the air intake tube 204 to provide air from outside to a replaceable vaporizer assembly inside the electronic cigarette 100. When the user rotates the mouthpiece 102 to a second predetermined angle in a different direction, the first air intake opening 1022 of the mouthpiece 102 misaligns with the first air intake opening 2041 of the air intake tube 204, and the second air intake opening 1022 of the mouthpiece 102 misaligns with the second air intake opening 2042 of the air intake tube 204 to shut off the air from outside to the replaceable vaporizer assembly inside the electronic cigarette 100.

Figure 2:
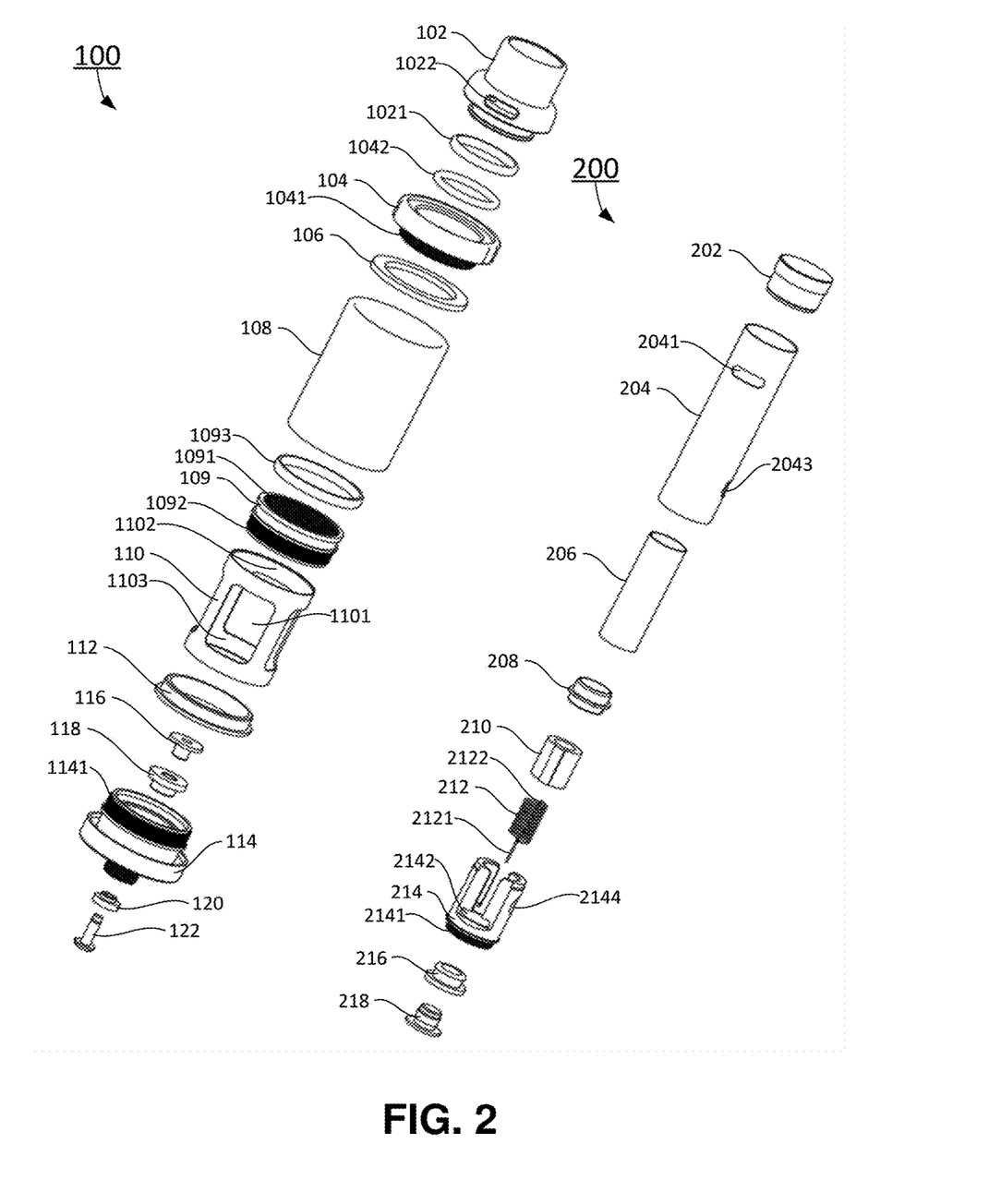
FIG. 2 is an exploded perspective view of the electronic cigarette having the replaceable vaporizer assembly and the top adjustable air intake according to certain embodiments of the present disclosure.
Figure 3:
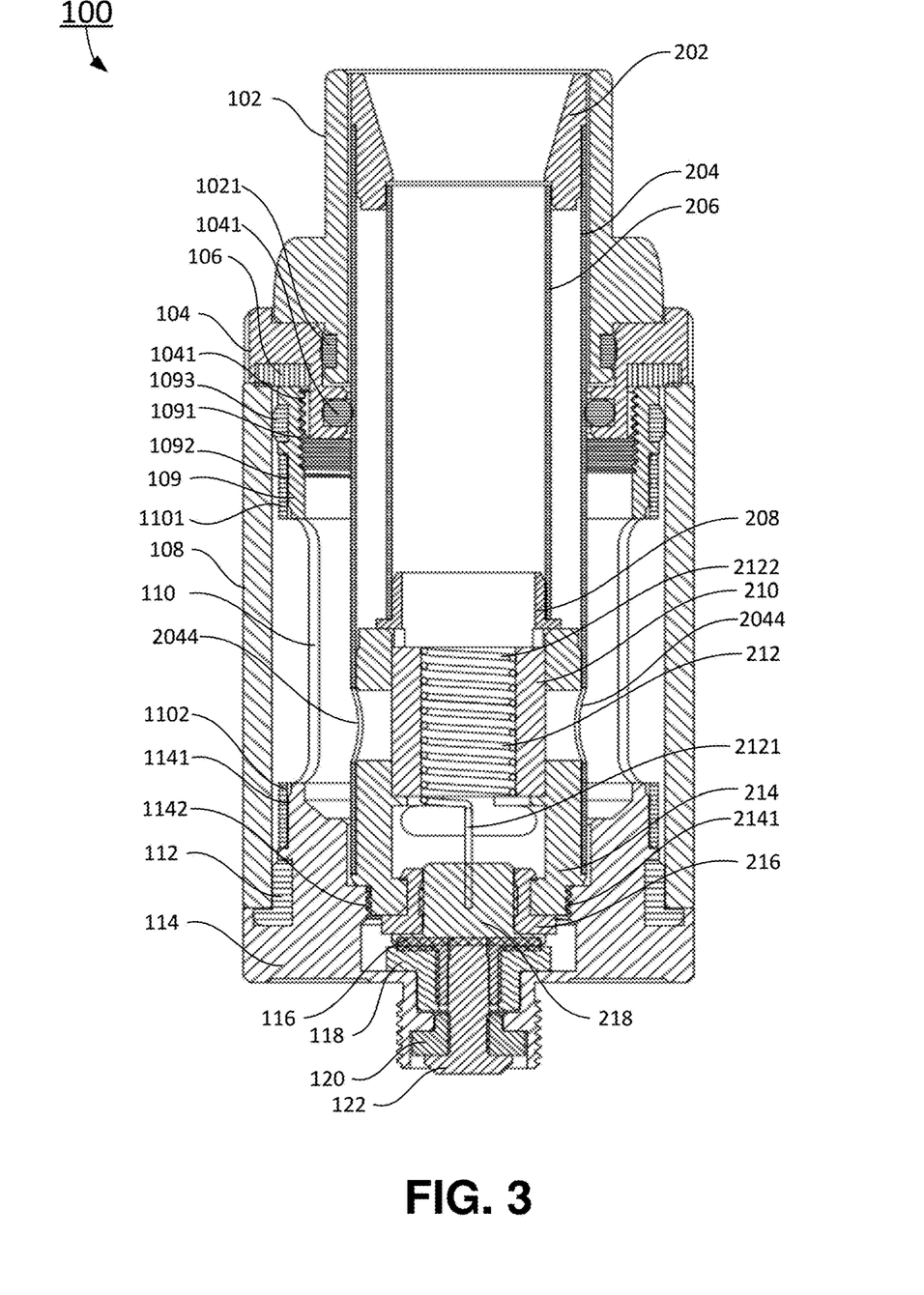
FIG. 3 is a detailed cross-sectional view of the electronic cigarette having the replaceable vaporizer assembly and the top adjustable air intake according to certain embodiments of the present disclosure.

Referring now to FIGS. 2 and 3, an exploded perspective view of the electronic cigarette 100 having a replaceable vaporizer assembly 200 and a detailed cross-sectional view of the electronic cigarette 100 are shown according to certain embodiments of the present disclosure.

In one aspect, the present disclosure relates to a replaceable vaporizer assembly 200 for electronic cigarettes. In certain embodiments, the replaceable vaporizer assembly 200 may include: a top vapor tube mount 202, an air intake tube 204, a vapor tube 206, a connecting ring 208, an E-liquid storage medium 210, a heating element 212, and a vaporizer assembly base 214.

In certain embodiments, the air intake tube 204 may define a first air intake opening 2041, a second air intake opening 2042, a first E-liquid opening 2043, and a second E-liquid opening 2044. The heating element 212 may include a positive terminal 2121 and a negative terminal 2122. The vaporizer assembly base 214 may define a first air gap 2142, a second air gap 2143, a first E-liquid opening 2144, and a second E-liquid opening 2145. The heating element 212 is installed inside the E-liquid storage medium 210. The E-liquid storage medium 210 is installed inside the vaporizer assembly base 214 between the connecting ring 208 and the vaporizer assembly base 214.

In certain embodiments, the air intake tube 204 is rotatable, and when in operation, the first E-liquid opening 2043 and the second E-liquid opening 2044 of the air intake tube 204 coincide the first E-liquid opening 2144 and the second E-liquid opening 2145 of the vaporizer assembly base 214 allowing that E-liquid outside of the air intake tube 204 to be in communication with the E-liquid storage medium 210 and the heating element 212 to generate E-liquid vapor.

In certain embodiments, the vapor tube 206 is positioned inside the air intake tube 204 between the top vapor tube mount 202 and the connecting ring 208 to form a cylindrical space between the vapor tube 206 and the air intake tube 204. An air passage is formed to provide air into an inside of the heating element 212 through the first air intake opening 2041 and the second air intake opening 2042, the cylindrical space between the vapor tube 206 and the air intake tube 204, the first air gap 2142 and the second air gap 2143.

In certain embodiments, the vaporizer assembly base 214 may include an external thread 2141 configured to threadedly connect to an internal thread 1142 of a vaporizer mounting base 114. Each of the external thread 2141 of the vaporizer assembly base 214 and the internal thread 1142 of the vaporizer mounting base 114 may include multiple threads. In one embodiment, the external thread 2141 of the vaporizer assembly base 214 and the internal thread 1142 of the vaporizer mounting base 114 may have double threads. In another embodiment, the external thread 2141 of the vaporizer assembly base 214 and the internal thread 1142 of the vaporizer mounting base 114 may have triple threads. The vaporizer mounting base 114 includes a positive terminal 122, a first insulation ring 120, a positive contact 116, and a second insulation ring 118. The positive terminal 122 is used to connect a positive terminal of the power connector from a power supply to the electronic cigarette 100. A negative terminal of the power connector from the power supply is connected to the electronic cigarette 100 through the vaporizer mounting base 114. The first insulation ring 120 and the second insulation ring 118 are used to insulate the positive terminal 122, and the positive contact 116 to prevent short circuit, as shown in FIG. 2 and FIG. 3.

In certain embodiments, the replaceable vaporizer assembly 200 may also include: a vaporizer positive terminal 218, and an insulation tube 216. The external thread 2141 of the vaporizer assembly base 214 forms a negative terminal and electrically coupled to the negative terminal 2122 of the heating element 212. The vaporizer positive terminal 218 is electrically coupled to the positive terminal 2121 of the heating element 212. The insulation tube 216 is positioned between the vaporizer assembly base 214 and vaporizer positive terminal 218 to provide insulation between the vaporizer positive terminal 218 and the vaporizer assembly base 214.

In certain embodiments, the heating element 212 may include multiple heating elements. In one embodiment, the heating element 212 may include two heating elements each of them electrically coupled in parallel to generate increased amount of E-liquid vapor. In another embodiment, the heating element 212 may include three heating elements each of them electrically coupled in serial to generate increased amount of E-liquid vapor.

In certain embodiments, the air intake tube 204 is sealed by a sealing ring 1042 of an E-liquid refill cap 104 to prevent E-liquid leakage.

In another aspect, the present disclosure relates to an electronic cigarette body 100. In certain embodiments, the electronic cigarette body 100 may include: a mouthpiece 102, an E-liquid storage tank 108, an E-liquid refill cap 104, a connector 110, a mounting ring 109, and a vaporizer mounting base 114.

In certain embodiments, the E-liquid storage tank 108 may include a top end and a bottom end. The E-liquid refill cap 104 is positioned on the top end of the E-liquid storage tank 108. The mounting ring 109 may include an internal thread 1091. The E-liquid refill cap 104 may include an external thread 1041. The external thread 1041 of the E-liquid refill cap 104 is configured to threadedly connect to the internal thread 1091 of the mounting ring 109.

In certain embodiments, the connector 110 may a first internal thread 1102 and a second internal thread 1103. The mounting ring 109 may include an external thread 1092. The second internal thread 1103 of the connector 110 is configured to threadedly connect to the external thread 1092 of the mounting ring 109.

In certain embodiments, the connector 110 may define multiple openings 1101. In one embodiment, the connector 110 may define a pair of openings 1101. In another embodiment, the connector 110 may define two pairs of openings 1101. These multiple openings 1101 may be used to allow E-liquid in the E-liquid storage tank 108 to enter the E-liquid storage medium 210, the heating element 212 through a first E-liquid opening 2144, and a second E-liquid opening 2145 of the vaporizer assembly base 214.

In certain embodiments, the vaporizer mounting base 114 may include an external thread 1141 configured to threadedly connect to the second internal thread 1103 of the connector 110, and an internal thread 1142 configured to threaded connected to an external thread 2141 of a vaporizer assembly base 214.

In certain embodiments, the mouthpiece 102 may include a first air intake opening 1022, and a second air intake opening 1023. The mouthpiece 102 is rotatable. When the mouthpiece 102 is rotated to a first predetermined angle such that the first air intake opening 1022 and the second air intake opening 1023 and a first air intake opening 2041 and a second air intake opening 2042 of an air intake tube 204 are respectively aligned to provide air to a replaceable vaporizer assembly 200 from outside of the electronic cigarette body 100. When the mouthpiece 102 is rotated to a second predetermined angle in a different direction such that the first air intake opening 1022 and the second air intake opening 1023 and the first air intake opening 2041 and the second air intake opening 2042 of the air intake tube 204 are respectively misaligned to shut off the air to the replaceable vaporizer assembly 200 from outside of the electronic cigarette body 100.

In yet another aspect, the present disclosure relates to an electronic cigarette. In certain embodiments, the electronic cigarette may include: an electronic cigarette body 100, and a replaceable vaporizer assembly 200. In certain embodiments, the electronic cigarette body 100 may include a mouthpiece 102, an E-liquid storage tank 108, an E-liquid refill cap 104, a mounting ring 109, a connector 110, and a vaporizer mounting base 114 having an internal thread 1142. The replaceable vaporizer assembly 200 may include an external thread 2141 of a vaporizer assembly base 214. The replaceable vaporizer assembly 200 may be replaced by removing the mouthpiece 102, unscrewing the replaceable vaporizer assembly 200 to detach the external thread 2141 of the vaporizer assembly base 214 from the internal thread 1142 of the vaporizer mounting base 114, pulling up the replaceable vaporizer assembly 200, replacing a new replaceable vaporizer assembly 200, and reinstalling the mouthpiece 102 back in place.

In certain embodiments, the heating element 212 may include multiple heating elements. In one embodiment, the heating element 212 may include two heating elements each of them electrically coupled in parallel to generate increased amount of E-liquid vapor. In another embodiment, the heating element 212 may include three heating elements each of them electrically coupled in serial to generate increased amount of E-liquid vapor.

In certain embodiments, the mouthpiece 102 may include a first air intake opening 1022, and a second air intake opening 1023. The mouthpiece 102 is rotatable. When the mouthpiece 102 is rotated to a first predetermined angle such that the first air intake opening 1022 and the second air intake opening 1023 and the first air intake opening and the second air intake opening of the air intake tube are respectively aligned to provide air to the replaceable vaporizer assembly 200 from outside of the electronic cigarette body 100. When the mouthpiece 102 is rotated to a second predetermined angle such that the first air intake opening 1022 and the second air intake opening 1023 and the first air intake opening 2041 and the second air intake opening 2042 of the air intake tube 204 are respectively misaligned to shut off the air to the replaceable vaporizer assembly 200 from outside of the electronic cigarette body 100.

In certain embodiments, the replaceable vaporizer assembly 200 may include: a top vapor tube mount 202, an air intake tube 204, a vapor tube 206, a connecting ring 208, an E-liquid storage medium 210, a heating element 212, and the vaporizer assembly base 214.

In certain embodiments, the air intake tube may define a first air intake opening, a second air intake opening, a first E-liquid opening, and a second E-liquid opening. The heating element 212 may include a positive terminal 2121 and a negative terminal 2122. The vaporizer assembly base 214 may define a first air gap 2142, a second air gap 2143, a first E-liquid opening 2144, and a second E-liquid opening 2145. The heating element is installed inside the E-liquid storage medium 210, and the E-liquid storage medium 210 is installed inside the vaporizer assembly base 214 between the connecting ring 208 and the vaporizer assembly base 214.

In certain embodiments, the replaceable vaporizer assembly 200 may include: a vaporizer positive terminal 218, and an insulation tube 216. The external thread 2141 of the vaporizer assembly base 214 forms a negative terminal and the external thread 2141 of the vaporizer assembly base 214 is electrically coupled to the negative terminal 2122 of the heating element 212. The vaporizer positive terminal 218 is electrically coupled to the positive terminal 2121 of the heating element 212. The insulation tube 216 is positioned between the vaporizer assembly base 214 and vaporizer positive terminal 218 to provide insulation between the vaporizer positive terminal 218 and the vaporizer assembly base 214.

In certain embodiments, the vapor tube 206 is positioned inside the air intake tube 204 between the top vapor tube mount 202 and the connecting ring 208 to form a cylindrical space between the vapor tube 206 and the air intake tube 204. An air passage is formed to provide air into an inside of the heating element 212 through the first air intake opening 2041 and the second air intake opening 2042 of the air intake tube 204, the cylindrical space between the vapor tube 206 and the air intake tube 204, the first air gap 2142 and the second air gap 2143 of the vaporizer assembly base 214.

Figure 4:
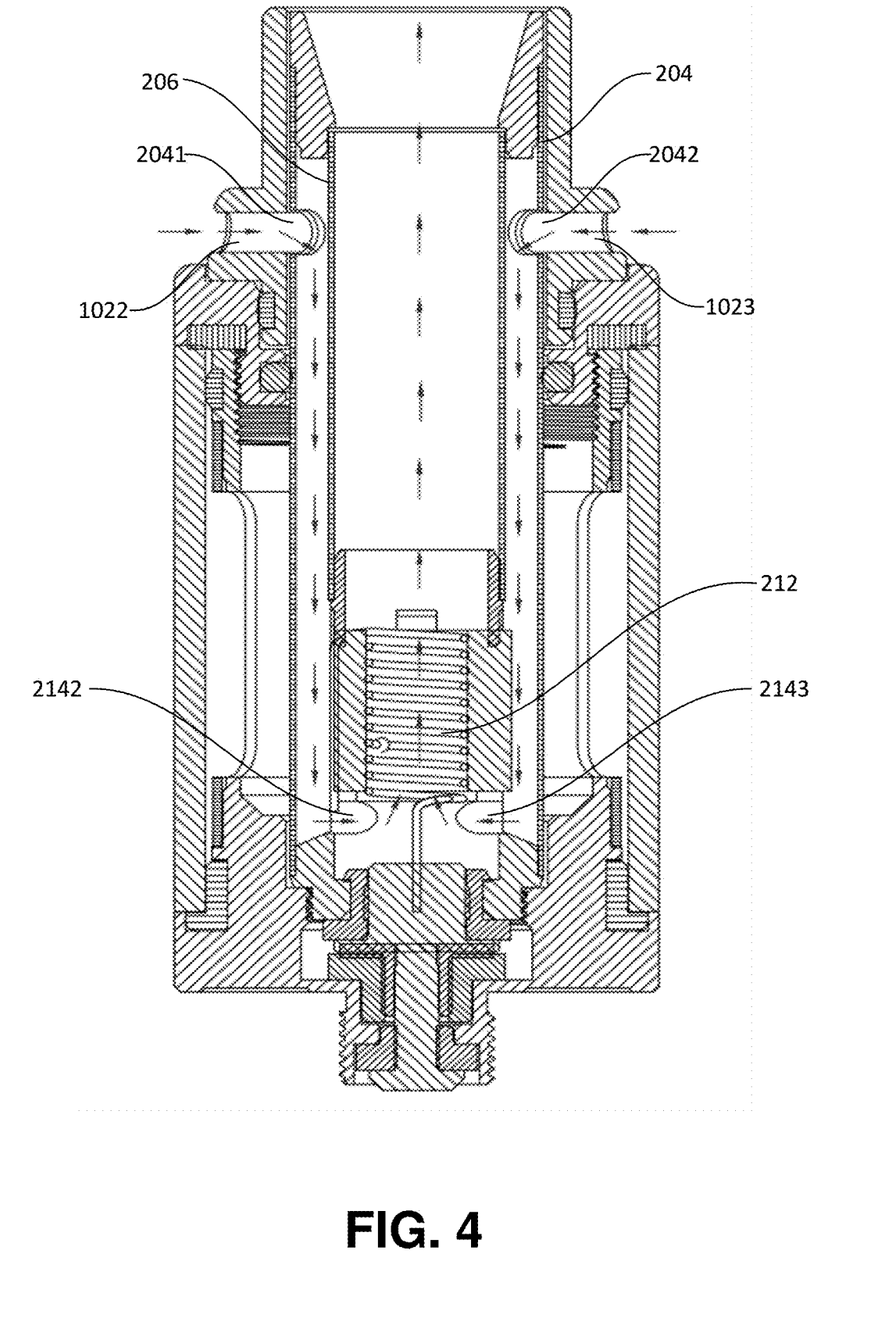
FIG. 4 is a detailed cross-sectional view of an air passage of the electronic cigarette showing air flow according to certain embodiments of the present disclosure.

Referring now to FIG. 4, a detailed cross-sectional view of an air passage of the electronic cigarette 100 is shown according to certain embodiments of the present disclosure. The air passage is marked by a series of arrows. Air outside of the electronic cigarette 100 enters the electronic cigarette 100 through the first air intake opening 1022 and the second air intake opening 1023 of the mouthpiece 102, the first air intake opening 2041 and the second air intake opening 2041 of the air intake tube 204. The air entered electronic cigarette 100 may go down through the cylindrical space between the air intake tube 204 and the vapor tube 206 due to a vacuum formed by sucking action of a user. The air then enters the replaceable vaporizer assembly through the first air gap 2142 and the second air gap 2143, and goes through the heating element 212 to form E-liquid vapor. The formed E-liquid vapor may travel upwards to the mouthpiece 102 through the vapor tube 206.

Figure 5A:
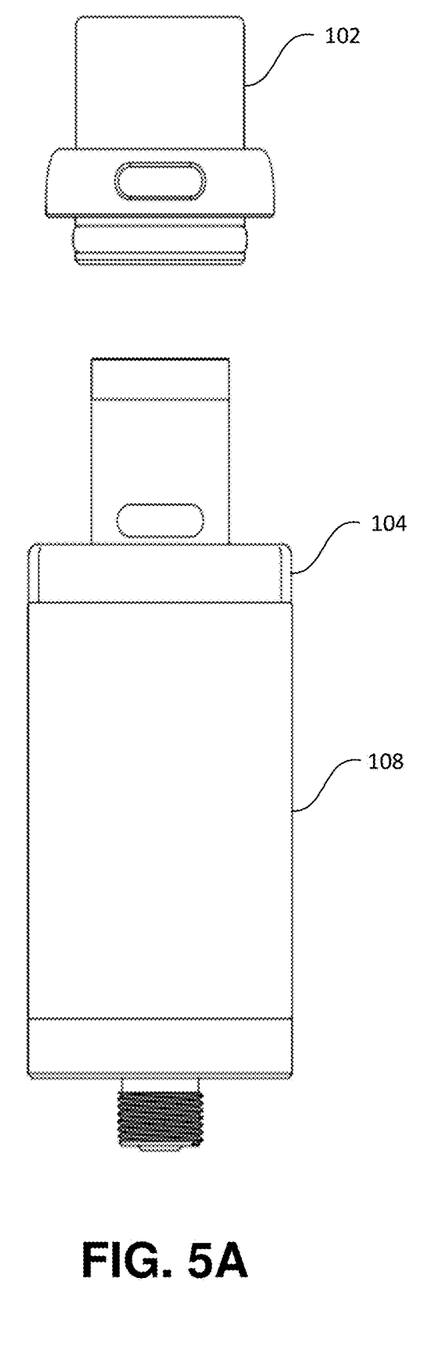
FIG. 5A shows an external view of an exemplary electronic cigarette having a mouthpiece removed for replacing the replaceable vaporizer assembly.
Figure 5B:
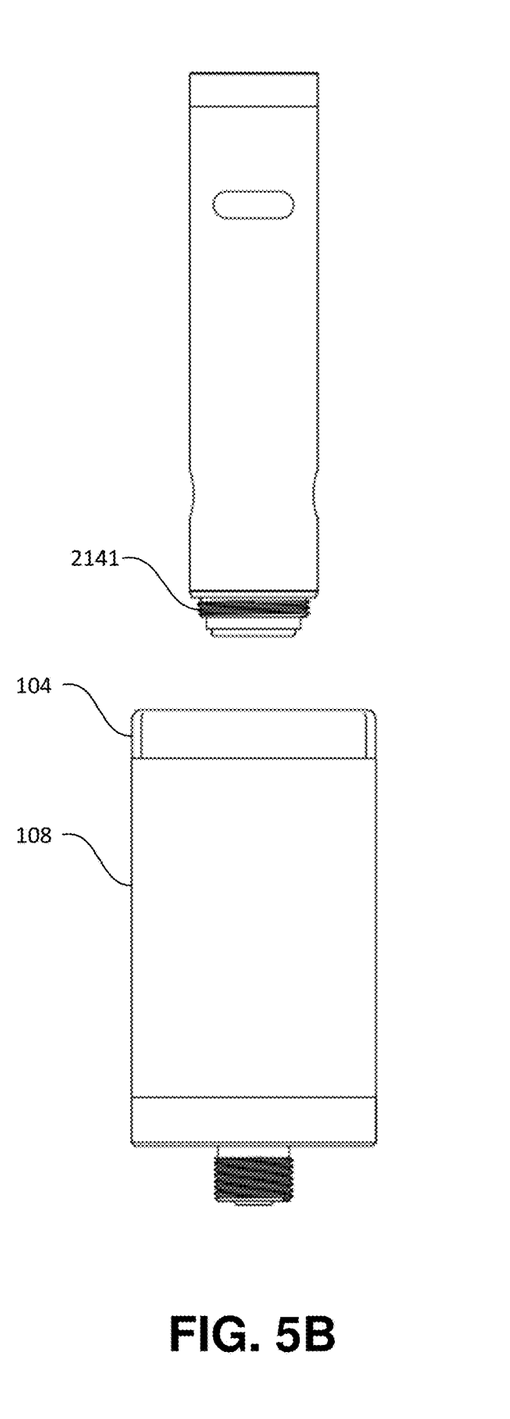
FIG. 5B shows an external view of the exemplary electronic cigarette with the replaceable vaporizer assembly detached from the electronic cigarette according to certain embodiments of the present disclosure.

Referring now to FIGS. 5A and 5B, an external view of the exemplary electronic cigarette 100 having a mouthpiece removed for replacing the replaceable vaporizer assembly 150, and having the replaceable vaporizer assembly 150 detached from the electronic cigarette 100 are shown, respectively, according to certain embodiments of the present disclosure.

In certain embodiments, the electronic cigarette may include: an electronic cigarette body 100, and a replaceable vaporizer assembly 200. In certain embodiments, the electronic cigarette body 100 may include a mouthpiece 102, an E-liquid storage tank 108, an E-liquid refill cap 104, and a vaporizer mounting base 114 having an internal thread 1142. The replaceable vaporizer assembly 200 may include an external thread 2141 of a vaporizer assembly base 214.

In certain embodiments, the mouthpiece 102 is slidedly installed on the electronic cigarette body 100. A sealing ring 1021 of the mouthpiece 102 may be used to ascertain reliable connection between the mouthpiece 102 and the electronic cigarette body 100. The replaceable vaporizer assembly 200 may be replaced by pulling the mouthpiece 102 upward to remove the mouthpiece 102 from the electronic cigarette body 100 as shown in FIG. 5A, rotating and unscrewing the replaceable vaporizer assembly 200 to detach the external thread 2141 of the vaporizer assembly base 214 from the internal thread 1142 of the vaporizer mounting base 114 as shown in FIG. 5B, pulling up the detached replaceable vaporizer assembly 200, replacing a new replaceable vaporizer assembly 200, and reinstalling the mouthpiece 102 back in place.

Such a replacement of replaceable vaporizer assembly 200 is easy, convenient, and without E-liquid contamination.

Figure 6A:
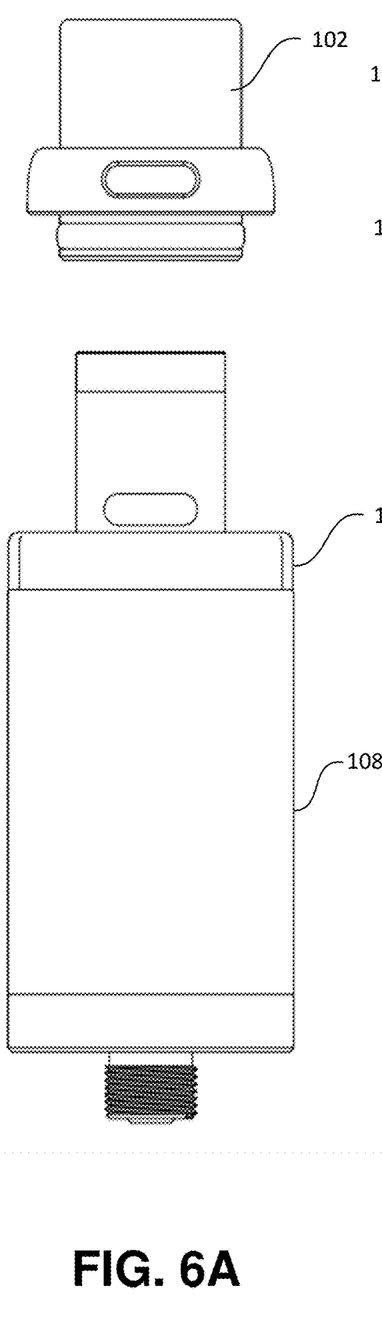
FIG. 6A shows an external view of the exemplary electronic cigarette before E-liquid refill.
Figure 6B:
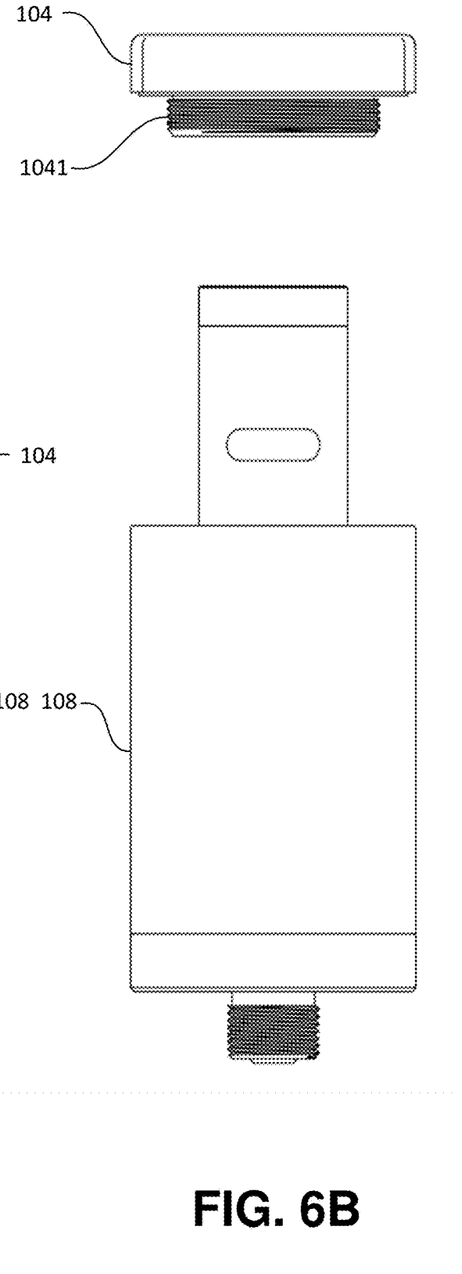
FIG. 6B shows an external view of the exemplary electronic cigarette with the mouthpiece and an E-liquid storage tank cover removed for E-liquid refilling according to certain embodiments of the present disclosure.

Referring now to FIGS. 6A and 6B, an external view of the exemplary electronic cigarette 100 before E-liquid refill, and the exemplary electronic cigarette 100 having the mouthpiece 102 and the E-liquid refill cap 104 removed for E-liquid refilling are shown, respectively, according to certain embodiments of the present disclosure.

In certain embodiments, the E-liquid storage tank 108 may be positioned between the E-liquid refill cap 104 and the vaporizer mounting base 114. The E-liquid storage tank 108 may be sealed by a first sealing ring 106 between the E-liquid refill cap 104 on the top end of the E-liquid storage tank 108 and a second sealing ring 112 between the bottom end of the E-liquid storage tank 108 and the vaporizer mounting base 114. The E-liquid in the E-liquid storage tank 108 is in communication with an E-liquid storage medium 210 through a first E-liquid opening 2043 and a second E-liquid opening 2044 of the air intake tube 204.

In certain embodiments, the E-liquid storage tank 108 is configured to store E-liquid between the top end and the bottom end of the E-liquid storage tank 108. When refilling E-liquid, a user may remove the mouthpiece 102, unscrew the E-liquid refill cap 104 to detach an external thread 1041 of the E-liquid refill cap 104 from the internal thread 1091 of the mounting ring 109 to open the top end of the E-liquid storage tank 108, and refill E-liquid into the E-liquid storage tank 108 from the opened top end of the E-liquid storage tank 108. Such refilling is clean, and without E-liquid contamination.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to activate others skilled in the art to utilize the disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims, the foregoing description and the exemplary embodiments described therein, and accompanying drawings.

What is claimed is:

1. A replaceable vaporizer assembly, comprising:
   a top vapor tube mount;
   an air intake tube defining a first air intake opening, a second air intake opening, a first E-liquid opening, and a second E-liquid opening;
   a vapor tube;
   a connecting ring;
   an E-liquid storage medium;
   a heating element having a positive terminal and a negative terminal; and
   a vaporizer assembly base defining a first air gap, a second air gap, a first E-liquid opening, and a second E-liquid opening,
   wherein the heating element is installed inside the E-liquid storage medium, and the E-liquid storage medium is installed inside the vaporizer assembly base between the connecting ring and the vaporizer assembly base.

2. The replaceable vaporizer assembly of claim 1, wherein the vapor tube is positioned inside the air intake tube between the top vapor tube mount and the connecting ring to form a cylindrical space between the vapor tube and the air intake tube, wherein an air passage is formed to provide air into an inside of the heating element through the first air intake opening and the second air intake opening, the cylindrical space between the vapor tube and the air intake tube, the first air gap and the second air gap of the vaporizer assembly base.

3. The replaceable vaporizer assembly of claim 1, wherein the heating element comprises a plurality of heating elements electrically coupled in parallel to generate increased amount of E-liquid vapor.

4. The replaceable vaporizer assembly of claim 1, wherein the air intake tube is sealed by a sealing ring of an E-liquid refill cap to prevent E-liquid leakage.

5. The replaceable vaporizer assembly of claim 1, wherein the vaporizer assembly base comprises an external thread configured to threadedly connect to an internal thread of a vaporizer mounting base.

6. The replaceable vaporizer assembly of claim 5, wherein each of the external thread of the vaporizer assembly base and the internal thread of the vaporizer mounting base comprises multiple threads.

7. The replaceable vaporizer assembly of claim 6, further comprising:
   a vaporizer positive terminal;
   an insulation tube, wherein the external thread of the vaporizer assembly base forms a negative terminal and electrically coupled to the negative terminal of the heating element, the vaporizer positive terminal is electrically coupled to the positive terminal of the heating element, and the insulation tube is positioned between the vaporizer assembly base and vaporizer positive terminal to provide insulation between the vaporizer positive terminal and the vaporizer assembly base.

8. An electronic cigarette body comprising:
a mouthpiece;
an E-liquid storage tank having a top end and a bottom end;
an E-liquid refill cap positioned on the top end of the E-liquid storage tank, wherein the E-liquid refill cap comprises an external thread;
a connector having a first internal thread, a second internal thread, wherein the connector defines a plurality of openings;
a mounting ring having an internal thread configured to threadedly connect to the external thread of the E-liquid refill cap, and an external thread configured to threadedly connect to the first internal thread of the connector; and
a vaporizer mounting base having an external thread configured to threadedly connect to the second internal thread of the connector, and an internal thread configured to threadedly connected to an external thread of a vaporizer assembly base.

9. The electronic cigarette body of claim 8, wherein the mouthpiece comprises a first air intake opening, and a second air intake opening, and the mouthpiece is rotatable, wherein when the mouthpiece is rotated to a first predetermined angle such that the first air intake opening and the second air intake opening and a first air intake opening and the second air intake opening of an air intake tube are respectively aligned to provide air to a replaceable vaporizer assembly from outside of the electronic cigarette body, and when the mouthpiece is rotated to a second predetermined angle such that the first air intake opening and the second air intake opening and the first air intake opening and the second air intake opening of the air intake tube are respectively misaligned to shut off the air to the replaceable vaporizer assembly from outside of the electronic cigarette body.

10. The electronic cigarette body of claim 8, wherein the E-liquid storage tank is positioned between the E-liquid refill cap and the vaporizer mounting base, sealed by a first sealing ring between the E-liquid refill cap on the top end of the E-liquid storage tank and a second sealing ring between the bottom end of the E-liquid storage tank and the vaporizer mounting base, wherein the E-liquid in the E-liquid storage tank is in communication with an E-liquid storage medium through a first E-liquid opening and a second E-liquid opening.

11. The electronic cigarette body of claim 10, wherein the E-liquid storage tank is configured to store E-liquid between the top end and the bottom end of the E-liquid storage tank, wherein when refilling E-liquid, a user may remove the mouthpiece, unscrew the E-liquid refill cap to detach the external thread of the E-liquid refill cap from the internal thread of the mounting ring to open the top and of the E-liquid storage tank, and refill E-liquid into the E-liquid storage tank from the opened top end of the E-liquid storage tank.

12. An electronic cigarette comprising:
an electronic cigarette body having a mouthpiece, an E-liquid storage tank, an E-liquid refill cap, a mounting ring, a connector, and a vaporizer mounting base having an internal thread, wherein the mouthpiece is mounted on the E-liquid storage tank, the E-liquid storage tank is screwed into the mounting ring, the mounting ring is mounted onto an upper portion of the connector, the mounting ring and the connector both fit in the E-liquid storage tank, a lower portion of the connector is mounted on an upper portion of the vaporizer mounting base, and a lower portion of the E-liquid storage tank receives the vaporizer mounting base; and
a replaceable vaporizer assembly having an external thread of a vaporizer assembly base,
wherein when replacing the replaceable vaporizer assembly a user removes the mouthpiece, unscrews the replaceable vaporizer assembly to detach the external thread of the vaporizer assembly base from the internal thread of the vaporizer mounting base, pulls up the replaceable vaporizer assembly, replaces a new replaceable vaporizer assembly, and reinstalls the mouthpiece back in place, wherein the mouthpiece comprises a first air intake opening, and a second air intake opening, and wherein the mouthpiece comprises a first air intake opening, and a second air intake opening, and the mouthpiece is rotatable, wherein when the mouthpiece is rotated to a first predetermined angle such that the first air intake opening and the second air intake opening and the first air intake opening and the second air intake opening of an air intake tube are respectively aligned to provide air to the replaceable vaporizer assembly from outside of the electronic cigarette body, and when the mouthpiece is rotated to a second predetermined angle such that the first air intake opening and the second air intake opening and the first air intake opening and the second air intake opening of the air intake tube are respectively misaligned to shut off the air to the replaceable vaporizer assembly from outside of the electronic cigarette body.

13. The electronic cigarette of claim 12, wherein each of the external thread of the vaporizer assembly base and the internal thread of the vaporizer mounting base comprises multiple threads.

14. The electronic cigarette of claim 12, wherein the heating element comprises a plurality of heating elements electrically coupled in parallel to generate increased amount of E-liquid vapor.

15. The electronic cigarette of claim 12, wherein the replaceable vaporizer assembly comprises:
a top vapor tube mount;
the air intake tube defining the first air intake opening, the second air intake opening, a first E-liquid opening, and a second E-liquid opening;
a vapor tube;
a connecting ring;
an E-liquid storage medium;
a heating element having a positive terminal and a negative terminal; and
the vaporizer assembly base defining a first air gap, a second air gap, a first E-liquid opening, and a second E-liquid opening,
wherein the heating element is installed inside the E-liquid storage medium, and the E-liquid storage medium is installed inside the vaporizer assembly base between the connecting ring and the vaporizer assembly base.

16. The electronic cigarette of claim 15, wherein the replaceable vaporizer assembly comprises:
a vaporizer positive terminal;
an insulation tube, wherein the external thread of the vaporizer assembly base forms a negative terminal and electrically coupled to the negative terminal of the heating element, the vaporizer positive terminal is electrically coupled to the positive terminal of the heating element, and the insulation tube is positioned between the vaporizer assembly base and vaporizer positive terminal to provide insulation between the vaporizer positive terminal and the vaporizer assembly base.

17. The electronic cigarette of claim 16, wherein the vapor tube is positioned inside the air intake tube between the top vapor tube mount and the connecting ring to form a cylindrical space between the vapor tube and the air intake tube, wherein an air passage is formed to provide air into an inside of the heating element through the first air intake opening and the second air intake opening, the cylindrical space between the vapor tube and the air intake tube, the first air gap and the second air gap of the vaporizer assembly base.

18. The electronic cigarette of claim 17, wherein the E-liquid storage tank is positioned between the E-liquid refill cap and the vaporizer mounting base, sealed by a first sealing ring between the E-liquid refill cap on the top end of the E-liquid storage tank and a second sealing ring between the bottom end of the E-liquid storage tank and the vaporizer mounting base, wherein the E-liquid in the E-liquid storage tank is in communication with the E-liquid storage medium through the first E-liquid opening and the second E-liquid opening.

19. The electronic cigarette of claim 18, wherein the E-liquid storage tank is configured to store E-liquid between the top end and the bottom end of the E-liquid storage tank, wherein when refilling E-liquid, a user may remove the mouthpiece, unscrew the E-liquid refill cap to detach an external thread of the E-liquid refill cap from an internal thread of the mounting ring to open the top and of the E-liquid storage tank, and refill E-liquid into the E-liquid storage tank from the opened top end of the E-liquid storage tank.

* * * * *